United States Patent [19]

Gupton et al.

[11] Patent Number: 4,503,262
[45] Date of Patent: Mar. 5, 1985

[54] PROCESS FOR THE PRODUCTION OF 2,6-DIISOPROPYLNAPHTHALENE DIHYDROPEROXIDE

[75] Inventors: B. Franklin Gupton, Virginia Beach; Edwin D. Little, Portsmouth, both of Va.

[73] Assignee: Virginia Chemicals, Inc., Portsmouth, Va.

[21] Appl. No.: 520,470

[22] Filed: Aug. 4, 1983

[51] Int. Cl.$^3$ .......................................... C07C 179/035
[52] U.S. Cl. .................................. 568/575; 568/569; 568/573; 568/574
[58] Field of Search ................. 568/569, 573, 575, 574

[56] References Cited

U.S. PATENT DOCUMENTS

| Re. 23,916 | 12/1954 | Lorand et al. | 568/575 |
| 2,656,394 | 10/1953 | Joris et al. | 568/575 |
| 2,664,448 | 12/1953 | Lorand et al. | 568/575 |
| 2,868,842 | 1/1959 | Closson et al. | 568/569 |
| 3,102,918 | 9/1963 | Heise | 568/569 |
| 3,939,211 | 2/1976 | Spector et al. | 568/575 |

FOREIGN PATENT DOCUMENTS 312846 10/1971 U.S.S.R. .............................. 568/573

Primary Examiner—Werren B. Lone
Attorney, Agent, or Firm—Depaoli & O'Brien

[57] ABSTRACT

A process is disclosed for the preparation of 2,6-dihydroisopropylnaphthalene, dihydroperoxide involving the oxidation of 2,6-diisopropylnaphthalene in the presence of a catalyst wherein the improvement comprises carrying out said oxidation in the presence of a $C_5$–$C_{14}$ aliphatic hydrocarbon solvent.

7 Claims, No Drawings

4,503,262

PROCESS FOR THE PRODUCTION OF 2,6-DIISOPROPYLNAPHTHALENE DIHYDROPEROXIDE

BACKGROUND OF THE INVENTION

This invention is directed towards an improvement in the process for the catalytic oxidation of alkyl naphthalenes, specifically 2,6-diisopropylnapthalene to the corresponding hydroperoxide where the improvement resides in carrying out the catalytic oxidation in the presence of a particular class of solvents.

DESCRIPTION OF THE PRIOR ART

It is well known in the art that dialkylnaphthalene including 2,6-diisopropylnaphthalene can be oxidized in the presence of a catalyst to the corresponding dihydroperoxide. In this connection, reference is made to U.S. Pat. No. Re. 23,916, the entire disclosure of which is incorporated by reference. Said patent teaches the catalytic oxidation of dialkylnaphthalenes utilizing various catalysts which are conventional in the art such as cobalt and manganese and also contains a specific teaching at column 3, lines 30 and following to the effect that compounds containing aromatic nucleii such as those derived from naphthalene, anthracene, and phenanthrene are also operable but some of these compounds being solids must be dissolved in a suitable solvent such as benzene during the liquid phase oxidation. It has now been discovered that, for reasons which are not fully understood, the oxidation of 2,6-diisopropylnaphthalene to the corresponding 2,6-dihydroperoxide is enhanced by using a $C_5$–$C_{14}$ aliphatic hydrocarbon as a solvent. In fact, not only is the rate of reaction enhanced, but also the yield of the desired product is enhanced and the purity of the desired product is enhanced due to the minimization of by-product formation.

DESCRIPTION OF PREFERRED EMBODIMENTS

As has heretofore been pointed out, the catalytic oxidation of 2,6-diisopropylnaphthalene to the corresponding 2,6-diisopropylnaphthalene hydroperoxide is known in the art and a typical process being represented in aformentioned U.S. Pat. No. Re. 23,916. It is also well known in the art that in order to preserve the hydroperoxide to prevent its decomposition that the catalytic oxidation should take place in a basic medium, i.e. see U.S. Pat. No. 4,120,902, the disclosure of which is incorporated herein by reference. Thus, it becomes immediately apparent that applicants' sole improvement over the prior art resides in the use of a specific class of solvents; namely, $C_5$–$C_{14}$ aliphatic hydrocarbons in carrying out said catalytic oxidation.

As is known in the art, the oxidation can be carried out using either molecular oxygen or any oxygen-containing gas such as air. The oxygen may also be furnished in mixtures of oxygen with nitrogen or other inert gases. Oxygen as used alone may be in the form of pure or commercially available oxygen. Air may be utilized either as it is readily available or as humidified up to the saturation point.

The rate of input of oxygen-containing gas may vary over a wide range depending upon the concentration of the oxygen in the gas, the activity of the catalyst, the pressure at which the oxidation is carried out and the efficiency of the dispersion. In general, the rate of input will vary from about one liter to about 1200 liters per hour per kilogram of the 2,6-diisopropyl naphthalene, a preferred range on this basis being from about 800 to 1000 liters per hour per kilogram.

The oxidation process of this invention is carried out in the presence of a catalytically active heavy metal compound, particularly such metals as manganese, cobalt, lead, iron, nickel, copper, vanadium, chromium and mercury. The oxides, hydroxides, or organic acid salts of any of these metals or combinations thereof which are soluble in said 2,6-diisopropylnaphthalene and/or in the $C_5$–$C_{14}$ aliphatic hydrocarbon may be employed. The heavy metal salts of organic acids are particularly useful as catalysts in accordance with this invention. Examples of such salts are metal butylphthalate, metal linoleate, manganese naphthenate, a mixture of manganese and lead acetates, cobalt linoleate, cobalt naphthenate, mixed lead-cobalt naphthenate, and the heavy metal resinates, such as manganese, lead or cobalt resinate. The resinates may be derived from any rosin acid, such as abietic, pimaric, dehydroabietic, dihydroabietic or tetrahydroabietic acid. Those oxidized oils obtained according to the process of this invention and containing preponderant amounts of hydroperoxides are useful in initiating the oxidation reaction by relieving inhibitions caused by harmful impurities. These oxidized oils, however, do not act as actual catalysts and are therefore highly desirable initiators for those oxidations which exhibit inhibition.

The concentration of the catalytically active heavy metal compound is critical. In general, the high hydroperoxide yield may be obtained if the concentration of the catalyst in solution in the oxidation reaction mixture is at any particular instant from about 0.01 to about 0.8 wt. % based on the 2,6-diisopropylnaphthalene. A preferable range on this basis is from about 0.02 to about 0.05 wt. %. Within the ranges of catalyst concentration, the amount of any particular catalyst will vary somewhat depending upon the metal content and activity of the catalyst. It is possible, for example, in the preparation of the heavy metal salts of organic acids to vary the amount of metal contained in the final salt, consequently smaller amounts of a salt containing a relatively high metal content will be needed in comparison to the same salt containing a smaller amount of the metal. Similarly the cobalt salts are more active than the manganese and lead salts, and the naphthenates are more active than the linoleates, which in turn are more active than the acetates. Consequently, a smaller amount of cobalt naphthenate, for example, will be needed than will be needed in the case of lead naphthenate or manganese linoleate. Relative to the hydroperoxide-rich oils which may be used to initiate the oxidation reaction, these oils may be used in amounts varying from about 1 to about 50% based on the alkyl-substituted aromatic organic compound, but a preferable range is from about 2 to about 20%.

The temperatures at which the oxidations are carried out also are quite critical in obtaining optimum yields of hydroperoxides. The temperatures which actually may be used, however, will depend on the pressure existing during the oxidations. Upon the basis of atmospheric pressure, the temperature should be in the range of about 50° to about 100° C., a more desirable range being between about 70° and about 90° C., and a particularly advantageous range being between about 75° C. to 85° C. The minimum temperature of 50° C. is necessary since the process of this invention utilizes low catalyst concentrations and the rate of reaction at, for example, room temperature, is too slow to be of commercial significance. On the other hand, if the temperature during oxidation is too high, the reaction occurs in such a manner as to result in excessive by-product formation.

The pressures which can be utilized during those oxidations carried out at greater than atmospheric pressure are limited only by equipment design. From a practical standpoint pressures from atmospheric up to about 800 pounds per square inch are feasible. A preferable range is from about atmospheric to about 100 pounds per square inch.

Since the reaction is heterogeneous, suitable agitation is necessary. It is particularly important to bring the air, oxygen, or other oxygen-containing gas into intimate contact with the liquid phase, and this may be effected by using high-speed stirrers, suitable nozzles, porous plates or their combinations.

The method utilized in recovery of the reaction products will vary depending upon the use to which the hydroperoxide is to be put. If the use of the hydroperoxide does not require separation of the hydroperoxide from other components, such as alcohols, ketones and unreacted starting material which may be present in the crude reaction mixture, the oily reaction product may be filtered through a layer of some filter aid to remove the catalyst by adsorption, then washed with dilute aqueous alkali and used either in the wet, slightly cloudy state for various purposes or after clarification and drying by filtration. The dilute aqueous alkali used in the washing step may be sodium hydroxide, sodium carbonate, sodium bicarbonate, and the like, the concentration of these alkalies in aqueous solution ranging from about 1 to about 10% but preferably from about 2 to about 5%. If it is desired, however, to obtain a highly concentrated hydroperoxide, the crude reaction product, after the alkali wash, may be stripped of unreacted hydrocarbon by distillation at pressures of about 1 to about 10 millimeters of mercury per square centimeter.

The oxidation according to this invention apparently proceeds by a peroxide mechanism. Thus, 2,6-diisopropylnaphthalene when contacted with molecular oxygen forms a hydroperoxide on the tertiary carbon atom of one of the isopropyl groups. In the presence of a small amount of catalyst utilized in accordance with this invention, a very small fraction of a hydroperoxide is decomposed resulting in the formation of free radicals which are sufficient to initiate the formation of more hydroperoxide molecules. If the concentration of the catalyst exceeds the amount specified in accordance with this invention, increasing amounts of hydroperoxide will be decomposed resulting in acceleration of the overall oxidation but decreasing the amount of undecomposed hydroperoxide at the expense of the formation of secondary byproducts.

As has heretofore been pointed out, it is also advantageous to carry out the catalytic oxidation in a basic medium in order to minimize the degradation of the hydroperoxide. The use of the basic medium is well known in the art as mentioned in previously referred to U.S. Pat. No. 4,120,902.

For reasons which are not completely understood, it has been found that the use of a $C_5$–$C_{14}$ aliphatic hydrocarbon, particularly normal heptane as the solvent for carrying out the catalytic oxidation of 2,6-diisopropylnaphthalene results in a higher rate of production, greater yield of product and a purer product due to the fact that by-products are minimized. Although heptane is stressed in the examples, other solvents within this range are also applicable, such as normal hexane, normal octane, decane, dodecane, etc.

The 2,6-diisopropylnaphthalene dihydroperioxide of this invention can be converted to the corresponding 2,6-dihydroxynaphthalene which is a known starting monomer for the production of polymers. The conversion of the dihydroperoxide to the corresponding dihydroxy compound is well known in the art and involves reaction of the hydroperoxide in an acidic medium. Techniques of this type are disclosed in U.S. Pat. Nos. 3,927,124; 3,884,983; 3,928,469; 3,923,908 and 3,900,423, the disclosures of which are incorporated herein by reference.

The following examples will illustrate the novel process of this invention.

In the examples which follow, Examples 1 and 2 represent the novel process of this invention, whereas Examples 3 and 4 represent the use of solvents outside the scope of this invention.

EXAMPLE 1

To a 500 ml Morton flask was added 0.02 g of cobalt naphthenate (6% cobalt), 50.0 g normal heptane, 50.0 g 2,6-diisopropylnaphthalene, 0.103 g 2,6-diisopropylnaphthalene dihydroperoxide and 1.0 g sodium carbonate. The mixture was heated to 80° C. and stirred mechanically (approximately 900 RPM). Oxygen was then sparged into the reaction mixture through a medium porous gas dispersion tube at a rate of 0.3 cubic meters per minute. After six hours, the reaction mixture was removed and treated with two 100 ml portions of 2% sodium hydroxide. The caustic phase was separated from the reaction mixture and sparged with carbon dioxide. The solid 2,6-diisopropylnaphthalene dihydroperoxide was filtered from the aqueous liquid and dried under vacuum. The organic phase was treated with carbon dioxide and the unreacted 2,6-diisopropylnaphthalene and monohydroperoxide were recycled. The estimated steady state yield was 63%. Product assay was 95.7%.

EXAMPLE 2

To a 500 ml Morton flask was added 0.104 g of cobalt acetate, 50.0 g normal heptane, 50.0 g 2,6-diisopropylnaphthalene, 0.104 g 2,6-diisopropylnaphthalene dihydroperoxide, 1.0 water, and 1.0 g sodium carbonate. The mixture was heated to 80° C. and stirred mechanically (approximate 900 RPM). Oxygen was sparged into the reaction mixture through a medium porous gas dispersion tube at a rate of 0.3 cubic meters per minute. After ten hours, the reaction mixture was removed and worked up as in Example 1. The estimated steady state yield was 68%. The product assay was 96.8%.

EXAMPLE 3

The procedure of Example 2 was repeated with the sole exception that 50 g of benzene were substituted for the 50 g of heptane. The estimated steady state yield was about 55%, the product assay was 74.6%. Quite obviously, the results dramatically illustrate excessive by-product formation due to the fact that the purity of the compound was drastically reduced. Analysis of some of the by-products indicated a substantial amount of naphthols thereby detracting from the purity of the desired product.

EXAMPLE 4

The process of Example 2 was repeated with the sole exception that 50 g of methylisobutyl ketones are substituted for the 50 g of heptane. The estimated steady state yield was 40%. The product assay was 64%.

A comparison of Examples 3 and 4 will show that although the yields were comparable as between bezene and the ketone, the purity was significantly lower, thereby demonstrating the unpredictability of the solvent effect. Again, as in Example 3, naphthols were detected thereby detracting from the purity of the desired product.

What is claimed is:

1. In a process for the conversion of 2,6-diisopropylnaphthalene to 2,6-diisopropylnaphthalene hydroperoxide wherein said 2,6-diisopropylnaphthalene is dissolved in an organic solvent and contacted with an oxygen-containing gas in a basic medium at elevated temperatures, which are in the range of about 50° C. to about 100° C. at atmospheric pressure, in the presence of a catalyst selected from the group consisting of heavy metal oxides, hydroxides, organic acid salts and mixtures thereof, the improvement which comprises using a $C_5$–$C_{14}$ aliphatic hydrocarbon as said organic solvent.

2. The process of claim 1 wherein said aliphatic hydrocarbon is n-heptane.

3. The process of claim 2 wherein said heavy metal is cobalt.

4. The process of claim 1 wherein said range is between about 70° C. and about 90° C.

5. The process of claim 1 wherein said range is between about 75° C. and about 85° C.

6. The process of claim 1 wherein said dissolved 2,6-diisopropylnaphthalene is contacted at pressures up to about 100 pounds per square inch.

7. The process of claim 1 wherein said dissolved 2,6-diisopropylnaphthalene is contacted at pressures up to about 800 pounds per square inch.

* * * * *